(12) United States Patent
DeLuca et al.

(10) Patent No.: US 7,563,783 B2
(45) Date of Patent: Jul. 21, 2009

(54) 2-METHYLENE-19-NOR-(20S-24S)-1α,25-DIHYDROXYVITAMIN-D$_2$

(75) Inventors: Hector F. DeLuca, Deerfield, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/352,454

(22) Filed: Feb. 10, 2006

(65) Prior Publication Data

US 2006/0183716 A1    Aug. 17, 2006

Related U.S. Application Data

(60) Provisional application No. 60/652,473, filed on Feb. 11, 2005.

(51) Int. Cl.
*A61K 31/59* (2006.01)
*C07C 401/00* (2006.01)

(52) U.S. Cl. ..................... 514/167; 552/653
(58) Field of Classification Search ............... 514/167; 552/653
See application file for complete search history.

(56) References Cited

U.S. PATENT DOCUMENTS 4,666,634 A    5/1987    Miyamoto et al.

(Continued)

OTHER PUBLICATIONS

Baggiolini, et al., "Stereocontrolled Total Synthesis of 1α,25-Dihydroxycholecalciferol and 1α,25-Dihydroxyergocalciferol," J. Org. Chem. 51, 3098 (1986).

(Continued)

*Primary Examiner*—Sabiha N. Qazi
(74) *Attorney, Agent, or Firm*—Foley & Lardner LLP

(57) ABSTRACT

Compounds of formula I are provided where $X^1$, $X^2$, and $X^3$ are independently selected from H or hydroxy protecting groups. Such compounds may be used in preparing pharmaceutical compositions and are useful in treating a variety of biological conditions.

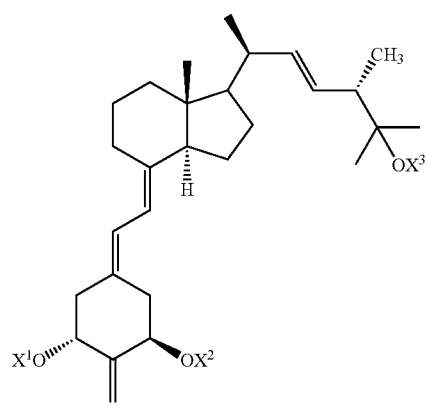

19 Claims, 5 Drawing Sheets

U.S. PATENT DOCUMENTS

| | | | |
|---|---|---|---|
| 5,086,191 | A | 2/1992 | DeLuca et al. |
| 5,536,713 | A | 7/1996 | Deluca et al. |
| 5,585,369 | A | 12/1996 | DeLuca et al. |
| 5,843,928 | A | 12/1998 | Deluca et al. |
| 5,945,410 | A | 8/1999 | DeLuca et al. |
| 6,384,087 | B1 | 5/2002 | Zemel et al. |
| 6,440,953 | B1 * | 8/2002 | DeLuca et al. ............... 514/167 |
| 6,479,474 | B2 * | 11/2002 | DeLuca et al. ............... 514/167 |
| 6,537,981 | B2 * | 3/2003 | DeLuca et al. ............... 514/167 |
| 6,566,352 | B1 | 5/2003 | DeLuca et al. |
| 6,579,861 | B2 | 6/2003 | DeLuca et al. |
| 6,627,622 | B2 | 9/2003 | DeLuca et al. |
| 6,673,782 | B2 * | 1/2004 | DeLuca et al. ............... 514/167 |
| 6,887,860 | B2 | 5/2005 | DeLuca et al. |
| 7,053,075 | B2 * | 5/2006 | DeLuca et al. ............... 514/167 |
| 7,094,774 | B2 * | 8/2006 | DeLuca et al. ............... 514/167 |
| 7,232,810 | B2 * | 6/2007 | DeLuca et al. ............... 514/167 |
| 7,259,143 | B2 * | 8/2007 | DeLuca et al. ................ 514/12 |
| 2002/0192264 | A1 | 12/2002 | Zemel et al. |
| 2004/0053813 | A1 * | 3/2004 | DeLuca et al. ................ 514/2 |
| 2004/0220418 | A1 | 11/2004 | DeLuca et al. |
| 2005/0065088 | A1 | 3/2005 | Thompson |
| 2005/0065133 | A1 | 3/2005 | Lee et al. |
| 2005/0065180 | A1 | 3/2005 | Lee |
| 2005/0070512 | A1 | 3/2005 | Lee |

OTHER PUBLICATIONS

Daniewski, et al., "A Novel Silylcopper Catalyst for the Reductive Bromination of Hajos Dione. Improved Preparation of a CD Synthon for the Synthesis of Vitamin D," J. Org. Chem. 66, 626-628 (2001).

Mascareñas, et al., "Studies of the Synthesis of Side-Chain Hydroxylated Metabolites of Vitamin D. 3. Synthesis of 25-Ketovitamin $D_3$ and 25-Hydroxyvitamin $D_3$," J. Org. Chem. 51, 1269 (1986).

Posner, et al., "2-Fluoroalkyl A-Ring Analogs of 1,25-Dihydroxyvitamin $D_3$-Stereocontrolled Total Synthesis via Intramolecular and Intermolecular Diels-Alder Cycloadditions. Preliminary Biological Testing," J. Org. Chem. 60, 4617 (1995).

Lythgoe, et al., "Calciferol and its Relatives. Part 22. A Direct Total Synthesis of Vitamin $D_2$ and Vitamin $D_3$," J. Chem. Soc. Perkin Trans. I, N6, 590 (1978).

Lythgoe, "Synthetic Approaches to Vitamin D and its Relatives," Chem. Soc. Rev. 9, 449 (1983).

Mincione, et al., "Improved Conversion of Vitamin $D_2$ into the Windaus Ketone and its Regioselective Hydroxylation via Organoboranes at $C_{26}$," Synth. Commun 19, 723 (1989).

Miyamoto, et al., "Synthetic Studies of Vitamin D Analogues. XIV. Synthesis and Calcium Regulating Activity of Vitamin $D_3$ Analogues Bearing a Hydroxyalkoxy Group at the 2β—Position," Chem. Pharm. Bull. 41(6), 1111 (1993).

Nishii, et al., "The Development of Vitamin $D_3$ Analogues for the Treatment of Osteoporosis," Osteoporosis Int. Suppl. 1, 190 (1993).

Okano, et al., "Regulatory Activities of 2β-(3-Hydroxypropoxy)-1α, 25-Dihydroxy-Vitamin $D_3$, a Novel Synthetic Vitamin $D_3$ Derivative, on Calcium Metabolism," Biochem. Biophys. Res. Commun. 163(3), 1444 (1989).

Ostrem, et al., "24- and 26-homo-1,25-dihydroxyvitamin $D_3$: Preferential activity in inducing differentiation of human leukemia cells HL-60 in vitro," Proc. Natl. Acad. Sci. USA, 84, 2610 (1987).

Perlman, et al., "1α, 25-Dihydroxy-19-Nor-Vitamin $D_3$, a Novel Vitamin D-related Compound with Potential Therapeutic Activitiy," Tetrahedron Lett. 31(13), 1823 (1990).

Perlman et al., "Novel Synthesis of 19-Nor-Vitamin D Compounds," Tetrahedron Lett. 32(52), 7663 (1991).

Peterson, et al., "Studies of the Ketone Obtained from the Ozonolysis of Vitamin D. Molecular Mechanics Calculations for It and Related Hydrindanones," J. Org. Chem. 51, 1948 (1986).

Posner, et al., "Stereocontrolled Total Synthesis of Calcitriol Derivatives: 1,25-Dihydroxy-2-(4'-hydroxybutyl)vitamin $D_3$ Analogs of an Osteoporosis Drug," J. Org. Chem. 59, 7855 (1994).

Sardina, et al., "Studies on the Synthesis of Side-Chain Hydroxylated Metabolites of Vitamin D. 2. Stereocontrolled Synthesis of 25-Hydroxyvitamin $D_2$," J. Org. Chem. 51, 1264 (1986).

Sicinski, R.R., et al., "New 1α,25-Dihydroxy-19-norvitamin $D_3$ Compounds of High Biological Activity: Synthesis and Biological Evaluation of 2-Hydroxymethyl, 2-Methyl, and 2-Methylene Analogues," J. Med. Chem., 41, 4662-4674 (1998).

Toh et al., "Studies on a Convergent Route to Side-Chain Analogues of Vitamin D: 25-Hydroxy-23-oxavitamin $D_3$," J. Org. Chem. 48, 1414 (1983).

Xue, B. et al., "Mechanism of intracellular calcium ($[Ca^{2+}]_i$) inhibition of lipolysis inhuman adipocytes," *The FASEB Journal*, vol. 15, Nov. 2001, pp. 2527-2529.

Shi, H. et al., "1α,25-Dihydroxyvitamin $D_3$ modulates human adipocyte metabolism via nongenomic action," *The FASEB Journal*, vol. 15, Dec. 2001, pp. 2751-2753.

Hiroshi, H. et al., Abstract of JP 03210156, Sep. 13, 1991.

* cited by examiner

2-METHYLENE-19-NOR-(20S-24S)-1α,25-DIHYDROXYVITAMIN-$D_2$

FIELD OF THE INVENTION

This invention relates to vitamin D compounds, and more particularly to 2-methylene-19-nor-(20S-24S)-1α,25-dihydroxyvitamin $D_2$ and to pharmaceutical formulations that include this compound. The invention also relates to the use of 2-methylene-19-nor-(20S-24S)-1α,25-dihydroxyvitamin $D_2$ or salts thereof in the preparation of medicaments for use in treating various diseases.

BACKGROUND OF THE INVENTION

The natural hormone, 1α,25-dihydroxyvitamin $D_3$ (also referred to as 1α,25-dihydroxycholecalciferol and calcitriol) and its analog in the ergosterol series, i.e. 1α,25-dihydroxyvitamin $D_2$, are known to be highly potent regulators of calcium homeostasis in animals and humans, and their activity in cellular differentiation has also been established, Ostrem et al., *Proc. Natl. Acad. Sci. USA*, 84, 2610 (1987). Many structural analogs of these metabolites have been prepared and tested, including 1α-hydroxyvitamin $D_3$, 1α-hydroxyvitamin $D_2$, various side chain homologated vitamins, and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies. The structure of 1α,25-dihydroxyvitamin $D_3$ and the numbering system used to denote the carbon atoms in this compound are shown below.

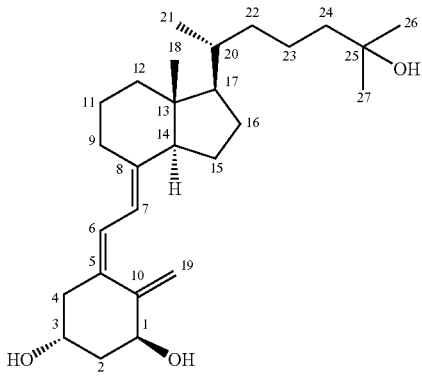

1α,25-Dihydroxyvitamin $D_3$=1α,25-Dihydroxycholecalciferol=Calcitriol

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., *Tetrahedron Lett.* 31, 1823 (1990); Perlman et al., *Tetrahedron Lett.* 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by the Chugai group as potential drugs for osteoporosis and as antitumor agents. See also Okano et al., *Biochem. Biophys. Res. Commun.* 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., *Chem. Pharm. Bull.* 41, 1111 (1993); Nishii et al., *Osteoporosis Int. Suppl.* 1, 190 (1993); Posner et al., *J. Org. Chem.* 59, 7855 (1994), and *J. Org. Chem.* 60, 4617 (1995)).

Various 2-substituted analogs of 1α,25-dihydroxy-19-nor-vitamin $D_3$ have also been synthesized, i.e. compounds substituted at the 2-position with hydroxy or alkoxy groups (DeLuca et al., U.S. Pat. No. 5,536,713), with 2-alkyl groups (DeLuca et al., U.S. Pat. No. 5,945,410), and with 2-alkylidene groups (DeLuca et al., U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-Hydroxy-2-methylene-19-nor-pregnacalciferol is described in U.S. Pat. No. 6,566,352 while 1α-hydroxy-2-methylene-19-nor-(20S)-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

SUMMARY OF THE INVENTION

The invention provides 2-methylene-19-nor-(20S-24S)-1α,25-dihydroxyvitamin $D_2$ and related compounds, pharmaceutical formulations that include 2-methylene-19-nor-(20S-24S)-1α,25-dihydroxyvitamin $D_2$, and the use of this compound in the preparation of medicaments for use in treating various disease states.

Therefore, in one aspect, the invention provides a compound having the formula I shown below

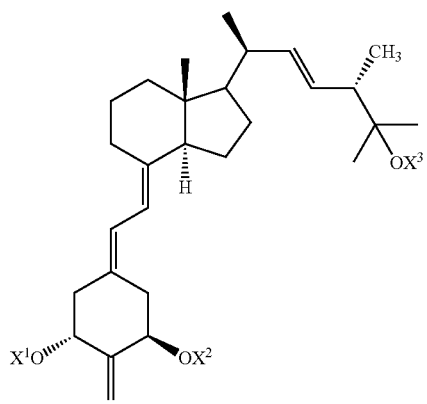

where $X^1$, $X^2$, and $X^3$ may be the same or different and are independently selected from H or hydroxy-protecting groups.

In some embodiments, $X^1$ and $X^2$ are both hydroxy protecting groups such as silyl groups. In some such embodiments, $X^1$ and $X^2$ are both t-butyldimethylsilyl groups. In other embodiments, $X^1$, $X^2$, and $X^3$ are all H such that the compound is 2-methylene-19-nor-(20S-24S)-1α,25-dihydroxyvitamin $D_2$ having the formula IA as shown below:

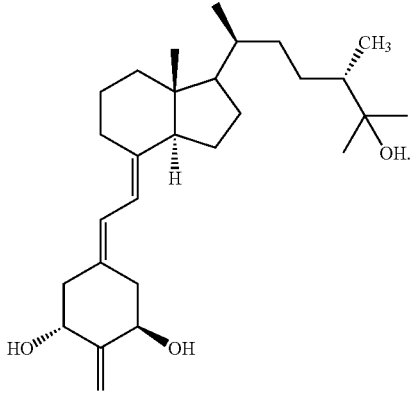

IA

In some such embodiments, the compound of formula IA is a compound of formula IB and has the structure shown below:

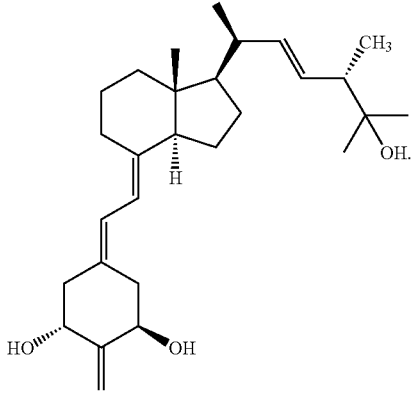

IB

The above compound exhibits a desired, and highly advantageous, pattern of biological activity. This compound is characterized by relatively high binding to vitamin D receptors, as compared to that of 1α,25-dihydroxyvitamin $D_3$, and similar intestinal calcium transport activity. The above compound is comparable to 1α,25-dihydroxyvitamin $D_3$ in it's ability to mobilize calcium from bone. Hence, this compound can be characterized as having some calcemic activity. Thus, it may be useful as a therapy for suppression of secondary hyperparathyroidism of renal osteodystrophy and for the treatment of other calcium imbalance disorders such as osteopenia.

The compound of the invention is also especially suited for treatment and prophylaxis of human disorders which are characterized by an imbalance in the immune system, e.g. in autoimmune diseases, including multiple sclerosis, lupus, diabetes mellitus, host versus graft reaction, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound of the invention.

The above compound is also characterized by relatively high cell differentiation activity. Thus, this compound also provides a therapeutic agent for the treatment of psoriasis, or as an anti-cancer agent, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

The compounds of the invention may be used to prepare pharmaceutical formulations or medicaments that include a compound of the invention in combination with a pharmaceutically acceptable carrier. Such pharmaceutical formulations and medicaments may be used to treat various biological disorders such as those described herein. Methods for treating such disorders typically include administering an effective amount of the compound or an appropriate amount of a pharmaceutical formulation or a medicament that includes the compound to a subject suffering from the biological disorder. In some embodiments, the subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the subject is a primate such as, in some embodiments, a human.

The compound may be present in a composition to treat the above-noted diseases and disorders in an amount from about 0.01 μg/gm to about 1 mg/gm of the composition, preferably from about 0.1 μg/gm to about 500 μg/gm of the composition, and may be administered topically, transdermally, orally, or parenterally in dosages of from about 0.01 μg/day to about 1 mg/day, preferably from about 0.1 μg/day to about 500 μg/day.

Further objects, features and advantages of the invention will be apparent from the following detailed description and drawings.

BRIEF DESCRIPTION OF THE DRAWINGS

FIG. 1 is a graph comparing the relative activity of (20S/24S) 2-$MD_2$ and 1,25$(OH)_2D_3$ to compete for binding with [$^3$H]-1,25-$(OH)_2$-$D_3$ to the full-length recombinant rat vitamin D receptor.

FIG. 2 is a graph comparing the percent HL-60 cell differentiation as a function of the concentration of (20S/24S) 2-$MD_2$ with that of 1,25$(OH)_2D_3$.

FIG. 3 is a graph comparing the in vitro transcription activity of (20S/24S) 2-$MD_2$ with that of 1,25$(OH)_2D_3$.

FIG. 4 is a bar graph comparing the bone calcium mobilization activity of (20S/24S) 2-$MD_2$ with that of 1,25$(OH)_2$ $D_3$.

FIG. 5 is a bar graph comparing the intestinal calcium transport activity of (20S/24S) 2-MD$_2$ with that of 1,25(OH)$_2$D$_3$.

DETAILED DESCRIPTION OF THE INVENTION

Figure 1:
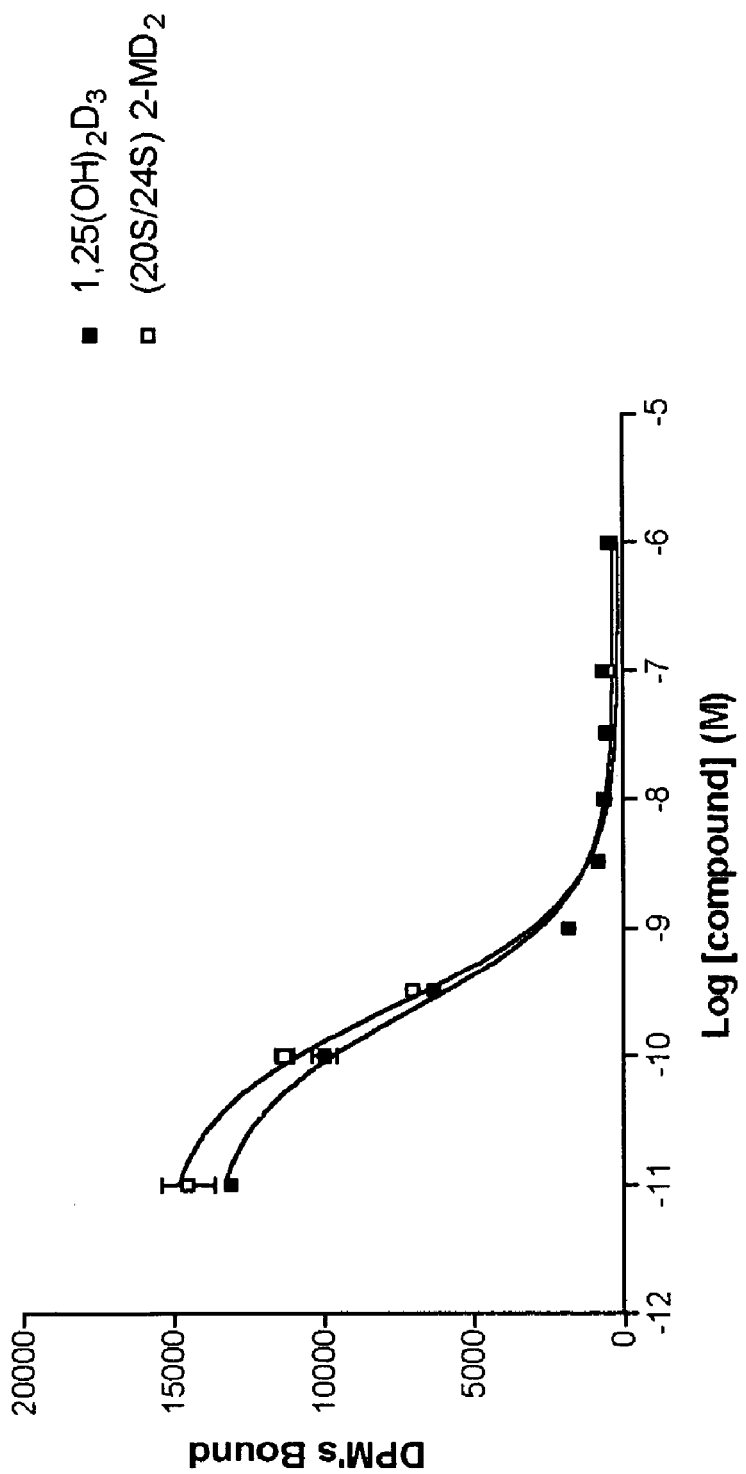
FIGS. 1-5 illustrate various biological activities of 2-methylene-19-nor-(20S-24S)-1α,25-dihydroxyvitamin $D_2$ (referred to as "(20S/24S) 2-$MD_2$" in the Figures) compared with those of the native hormone 1α,25-dihydroxyvitamin $D_3$ (referred to as "1,25$(OH)_2D_3$" in the Figures).

2-Methylene-19-nor-(20S-24S)-1α,25-dihydroxyvitamin D$_2$ was synthesized, and tested, and found to be useful in treating a variety of biological conditions as described herein. Structurally, this compound has the formula IA as shown below:

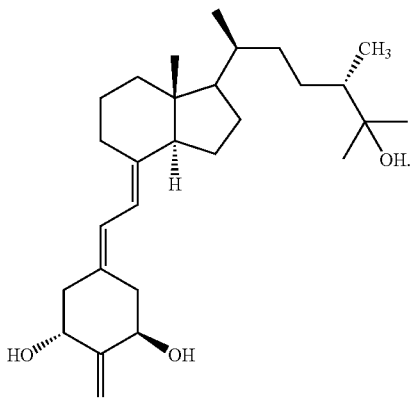

IA

Preparation of 2-methylene-19-nor-(20S-24S)-1α,25-dihydroxyvitamin D$_2$ can be accomplished by condensing an appropriate bicyclic Windaus-Grundmann type ketone (II) with the allylic phosphine oxide III followed by deprotection (removal of the Y$_1$ and Y$_2$ groups).

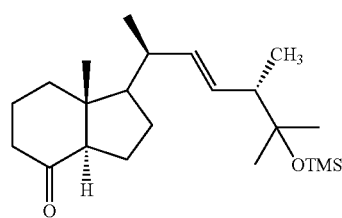

II

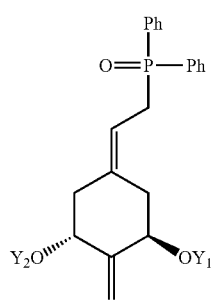

III

In phosphine oxide III, Y$_1$ and Y$_2$ are preferably hydroxy-protecting groups such as silyl protecting groups. The t-butyldimethylsilyl (TBDMS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans. I*, 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al., U.S. Pat. No. 5,843,928 all of which are hereby incorporated by reference in their entirety and for all purposes as if fully set forth herein).

Phosphine oxide III is a convenient reagent that can be used to prepare a large number of 19-nor vitamin D compounds and may be prepared according to the procedures described by Sicinski et al., *J. Med. Chem.*, 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191. Scheme I shows the general procedure for synthesizing phosphine oxide III as outlined in U.S. Pat. No. 5,843,928 which is hereby incorporated by reference in its entirety as if fully set forth herein. Modification of the method shown in Scheme I may be used to produce a large number of vitamin D analogs as will be apparent to those skilled in the art. For example, a wide variety of phosphonium compounds may be used in place of the MePh$_3$P$^+$Br$^-$ used to convert ketone B to alkene C. Examples of such compounds include EtPh$_3$P$^+$Br$^-$, PrPh$_3$P$^+$Br$^-$, and compounds generally prepared by reaction of triphenylphosphine with an alkyl halide, an alkenyl halide, a protected-hydroxyalkyl halide, and a protected hydroxyalkenyl halide. Alkenes prepared using this procedure may then be carried through to prepare a phosphine oxide in an analogous manner to that used to prepare phosphine oxide H in Scheme I. Alternatively, an alkene analogous to compound C of Scheme I may be reduced with (Ph$_3$P)$_3$RhCl and H$_2$ to provide other vitamin D analogs. See U.S. Pat. No. 5,945,410 and Sicinski, R. R. et al., *J. Med. Chem.*, 41, 4662-4674 (1998) both of which are hereby incorporated by reference in their entireties and for all purposes. Therefore, the procedure for forming the phosphine oxide shown in Scheme I may be used to prepare a wide variety of vitamin D analogs in addition to the compound of the present invention.

Scheme I

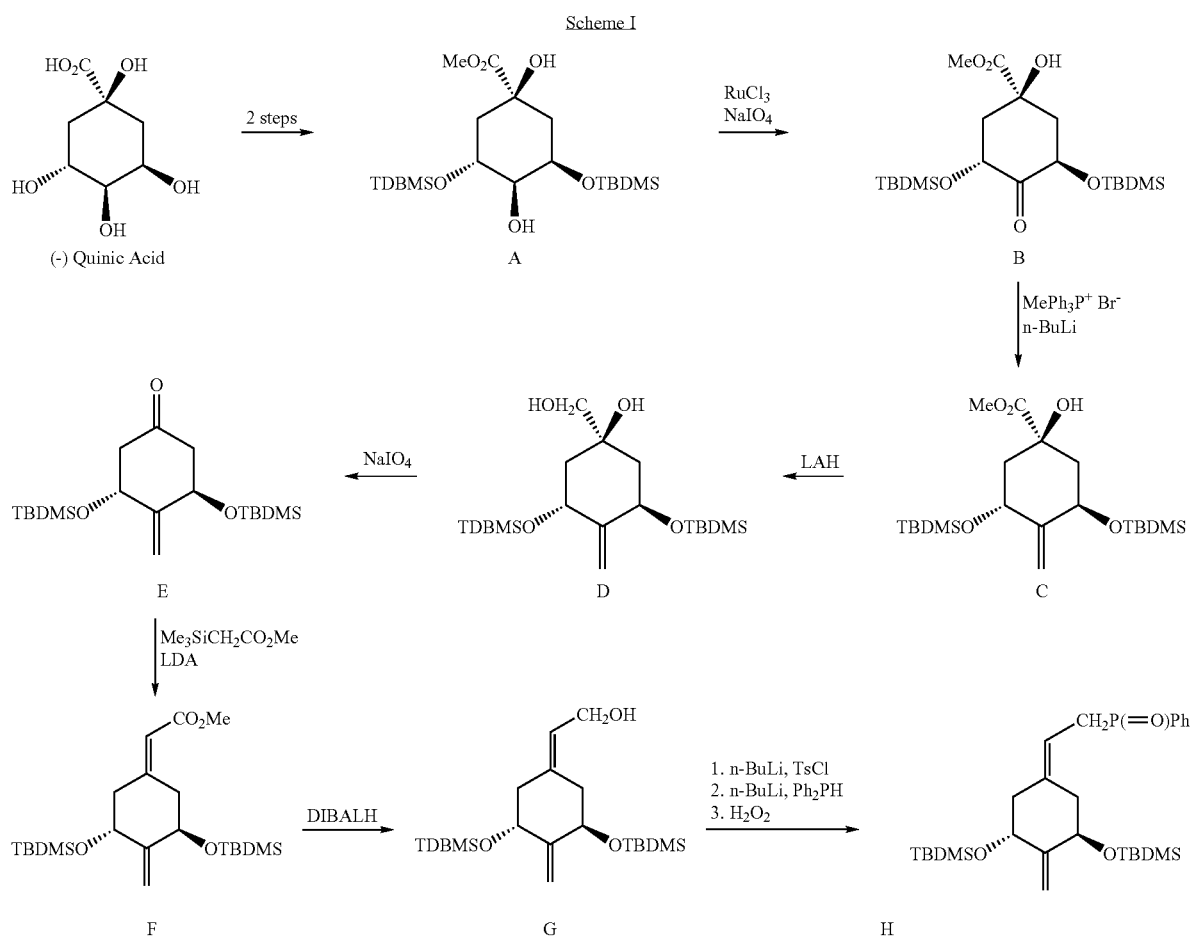

Hydraindanones of structure II can prepared by known methods or adapted methods as will be readily apparent to one of skill in the art and described herein. Specific examples of some important bicyclic ketones used to synthesize vitamin D analogs are those described in Mincione et al., *Synth. Commun.* 19, 723, (1989); and Peterson et al., *J. Org. Chem.* 51, 1948, (1986).

An overall process for synthesizing 2-alkylidene-19-nor-vitamin D compounds is illustrated and described in U.S. Pat. No. 5,843,928 which is hereby incorporated by reference in its entirety and for all purposes as if fully set forth herein.

As used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groups such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

EXAMPLES

Synthesis of 2-methylene-19-nor-(20S-24S)-1α,25-dihydroxyvitamin $D_2$

The synthesis and characteristics of various 19-nor vitamin D analogs is described in numerous United States patents including U.S. Pat. Nos. 5,843,928, 6,627,622, 6,579,861, 5,086,191, 5,585,369, and 6,537,981. Each of the above-described references is hereby incorporated by reference in its entirety and for all purposes as if fully set forth herein.

Compounds of formula I, formula IA, and formula IB were prepared using the methods shown in Schemes I, IIA, and IIB. Compound 1 is obtained by ozonolysis of ergocalciferol or vitamin $D_2$ as described by Sicinski et al. (*J. Med. Chem.* 41, 4662-4672, 1998). Compound 1 is reduced with borohydride to produce the dihydroxy compound 2. These reactions can be followed by thin layer chromatography (TLC) using a solvent system of 10% ethyl acetate in hexane. Treatment of 2 with acetic anhydride in pyridine provides the acetate compound 3. Compound 3 is then treated with triethylsilyl trifluoromethane sulfonate followed by base hydrolysis (heating with KOH in methanol) to yield compound 4. Again, these reactions are followed by the same TLC system as above. Compound 4 is oxidized with sulfur trioxide in pyridine, dimethylsulfoxide and triethylamine to provide 5. The reaction is followed by TLC using 10% in acetic acid. Treatment of 5 with sodium bicarbonate to epimerize the compound followed by reduction with sodium borohydride in methanol provides alcohol 6 and is detected by TLC with 20% ethyl acetate in hexane. Compound 6 is then oxidized using the reagents shown in Scheme IIA to produce compound 7 which is in turn was reacted with the stereospecific sulfone (compound 8) in the presence of n-BuLi (Scheme IIB). Sulfone 8 was prepared using starting materials obtained from the Aldrich Chemical Company (Milwaukee, Wis.) using the procedures disclosed in U.S. Pat. No. 5,750,746, which issued to DeLuca et al. on May 12, 1998. Acetylation of this compound was performed using acetic anhydride and pyridine resulting in compound 9, which was confirmed by TLC (10% ethyl acetate in hexane). Compound 9 was then converted to compound 10, by reaction with a sodium amalgam. The presence of compound 10, was confirmed by TLC (10% ethyl acetate in hexane). Deprotection of compound 10 was accomplished using pyridinium p-toluene sulfonate, and the reaction followed by TLC with 35% ethyl acetate in hexane. Oxidation of compound 11 was accomplished by reaction with pyridinium chlorochromate. A trimethylsilyl group was then added in the presence of imidazole to provide compound 13. Products 12 and 13 were detected by TLC with 35% ethyl acetate in hexane. A Wittig-Horner condensation of the protected Grundmann's Ketone (Compound 13) with the phosphine oxide (Compound 14) in the presence of n-BuLi was performed. The resulting product (Compound 15) was confirmed by TLC (20% ethyl acetate in hexane). Finally, the target compound (Compound 16) was generated by deprotection in the presence of tetrabutyl ammonium fluoride. The reaction was followed by TLC with 10% methanol in chloroform. Additional confirmation of the end product is described below:

Scheme IIA

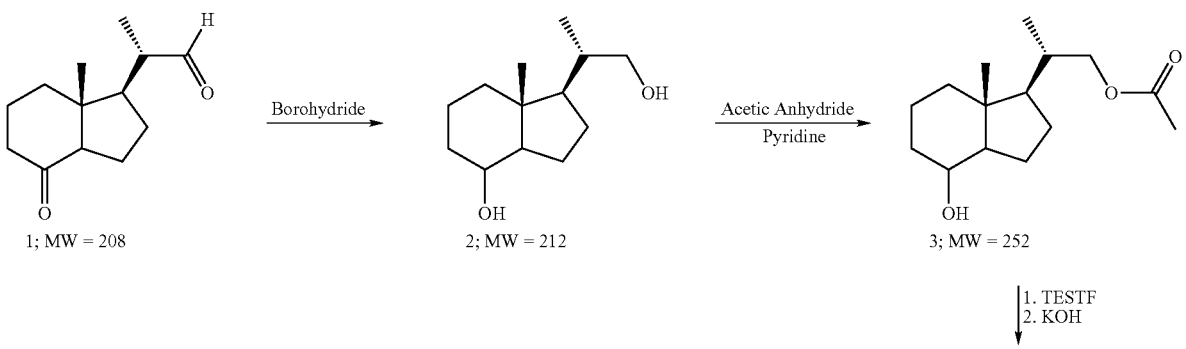

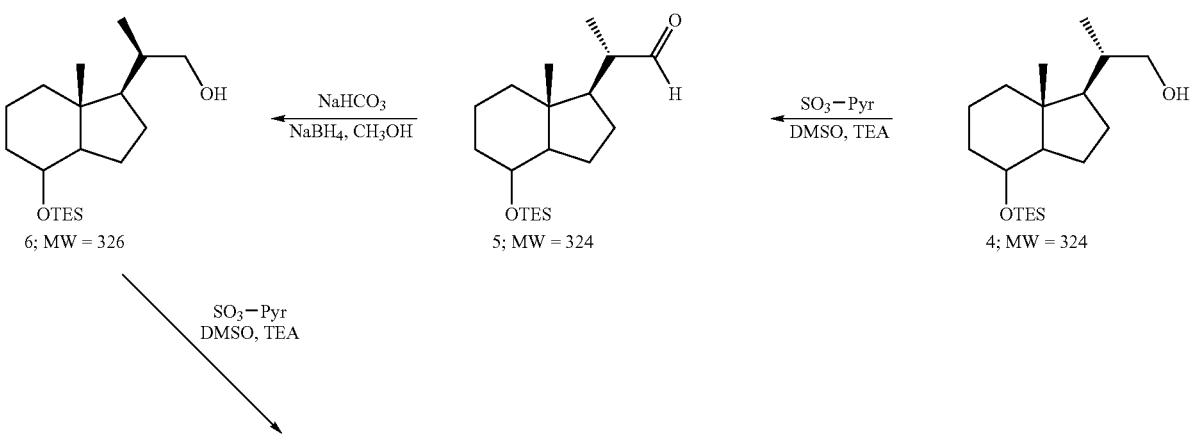

-continued
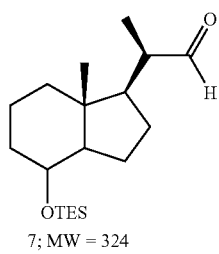
7; MW = 324
Scheme IIB
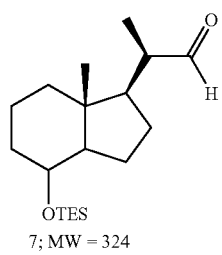
7; MW = 324
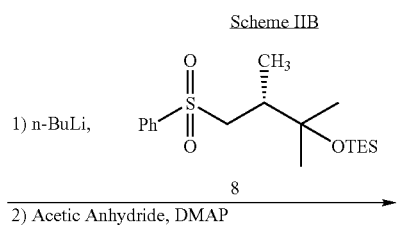
1) n-BuLi, 8
2) Acetic Anhydride, DMAP
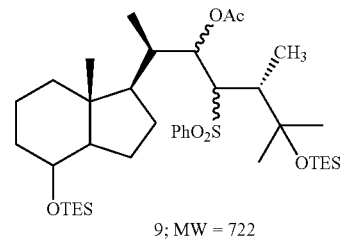
9; MW = 722
↓ Na(Hg)
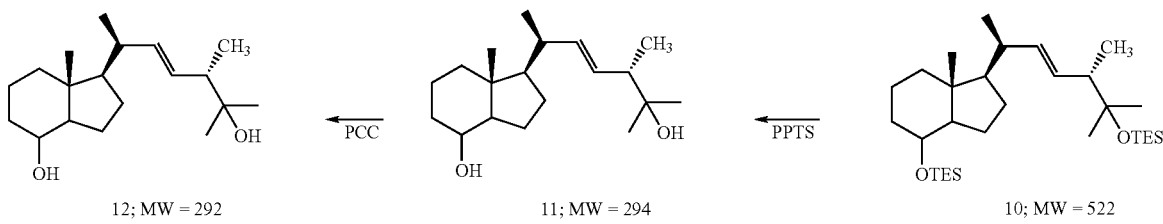
12; MW = 292 ← PCC ← 11; MW = 294 ← PPTS ← 10; MW = 522
↓ TMS - Imidazole
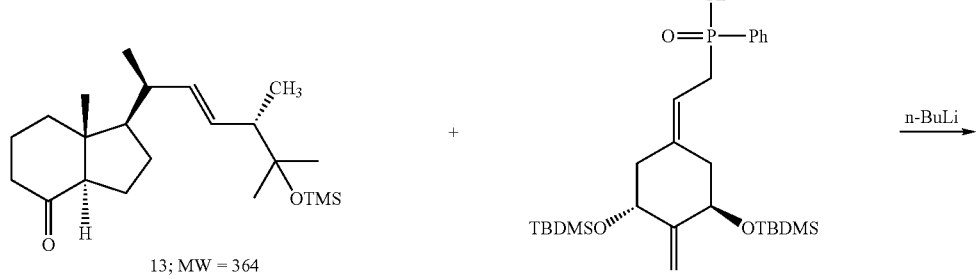
13; MW = 364
+
n-BuLi →

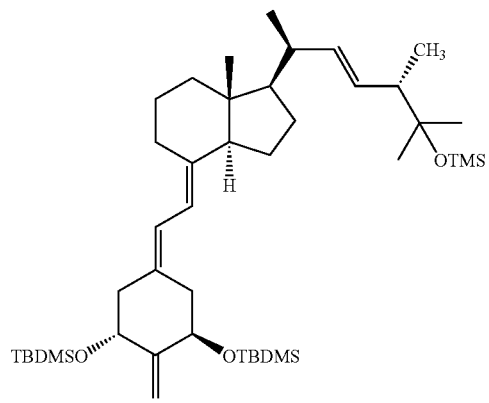

15; MW = 729

↓ TBAF

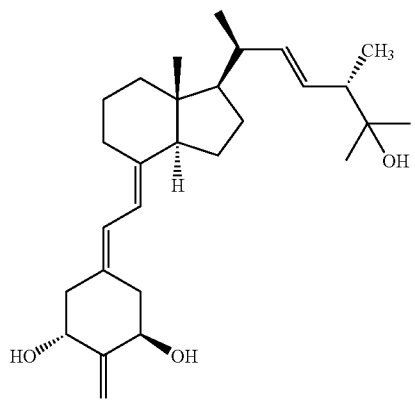

16; MW = 428

2-methylene-19-nor-(20S-24S)-1α,25-dihydroxyvitamin D$_2$ $^1$H NMR (300 MHz, CDCl$_3$) δ 0.524 (3H, s, 18-H$_3$), 0.938 (3H, d, J=6.6 Hz, 21-H$_3$), 0.995 (3H, d, J=7.2 Hz, 28-H$_3$), 1.142 and 1.169 (3H and 3H, each s, 26- and 27-H$_3$), 1.8-2.2 (5H, br m), 2.28 (1H, dd, J=13.2, 8.4 Hz, 10α-H), 2.33 (1H, dd, J=13.5, 6.3 Hz, 4β-H), 2.57 (1H, dd, J=13.5, 3.9 Hz, 4α-H), 2.80 (1H, m, 9β-H), 2.85 (1H, dd, J=13.2, 4.5 Hz, 10β-H), 4.49 (2H, m, 1β- and 3α-H), 5.09 and 5.11 (1H and 1H, each s, =CH$_2$), 5.33-5.49 (2H, br m, 22- and 23-H), 5.88 and 6.35 (1H and 1H, each d, J=11.4 Hz, 7- and 6-H); MS (APCl) m/z 411 [(M+H)$^+$ —H$_2$O ].

BIOLOGICAL ACTIVITY

Vitamin D Receptor Binding

Test Material

Protein Source

Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and λ$_{max}$=265 nm; Analogs: molar extinction coefficient=42,000 and λ$_{max}$=252 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapatite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol ($\leq 0.2\%$) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; *J. Exp. Med.* 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was, measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (0.47% Ca) diet+AEK for one week followed by Diet 11 (0.02% Ca)+AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Figure 2:
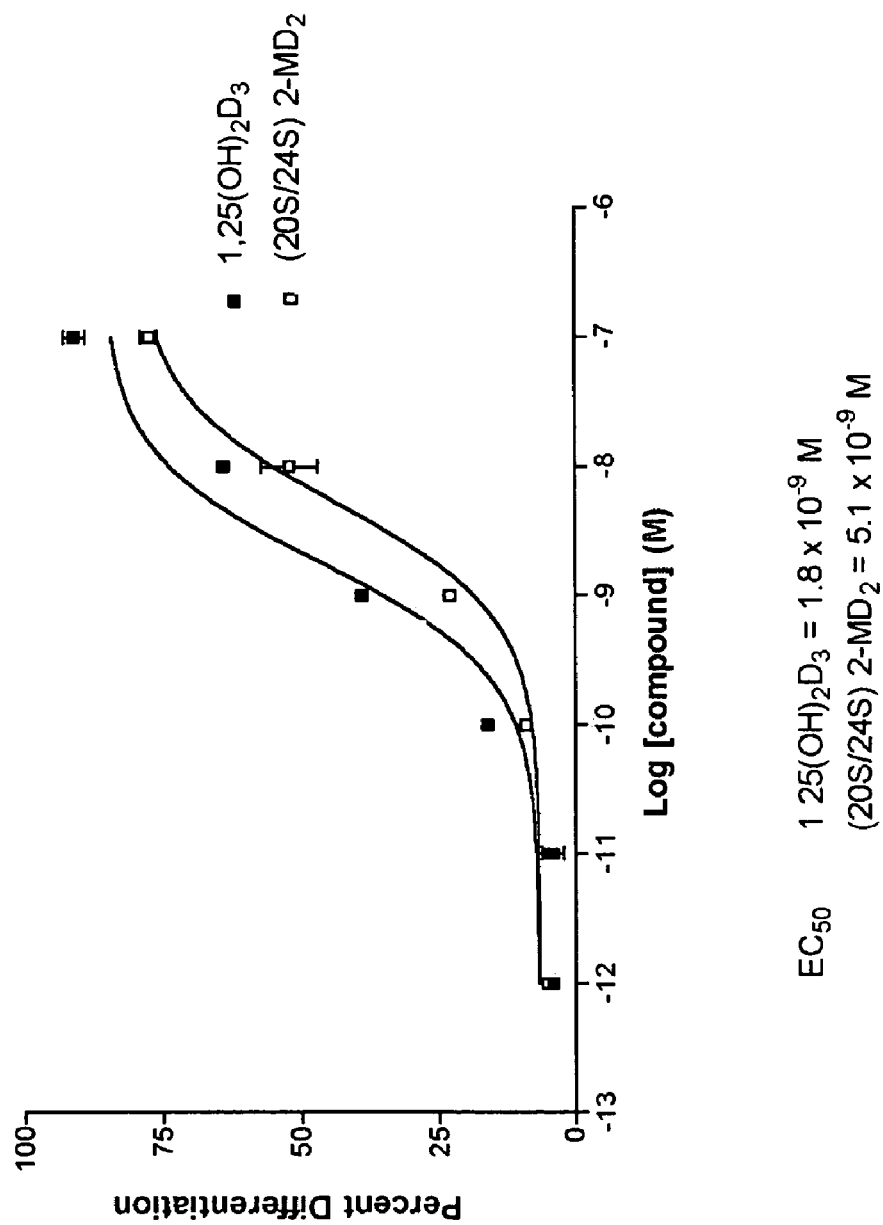
Figure 3:
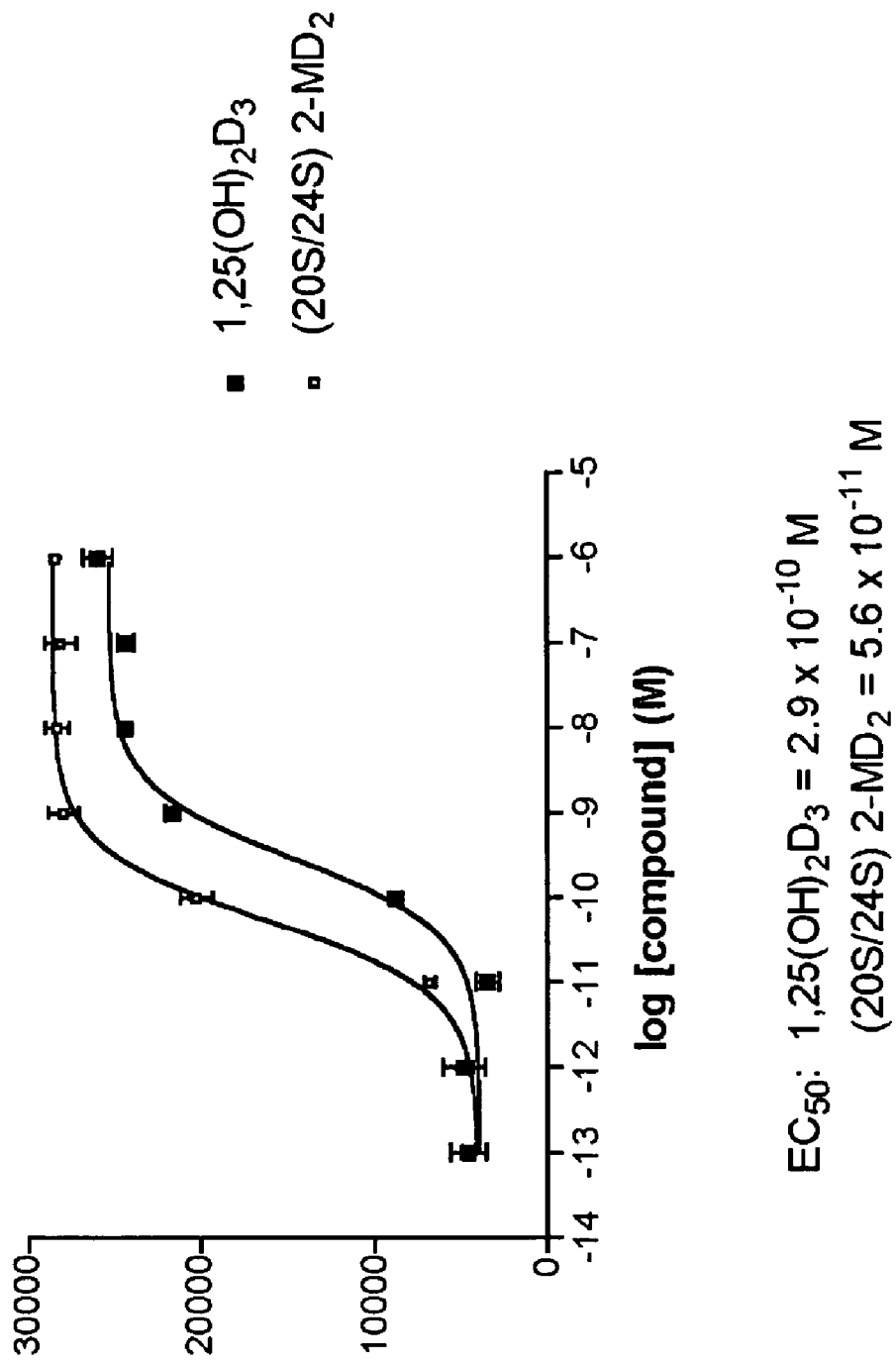
Figure 4:
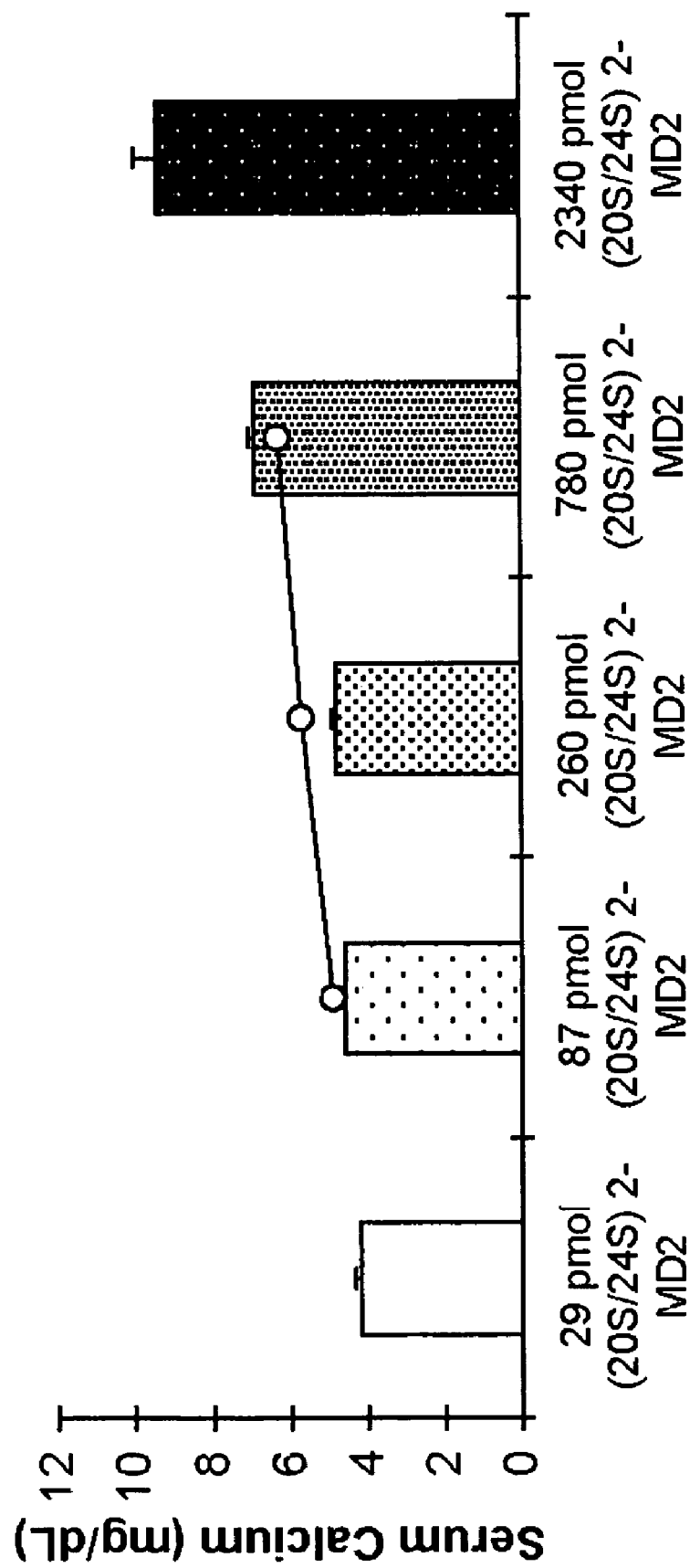
Figure 5:
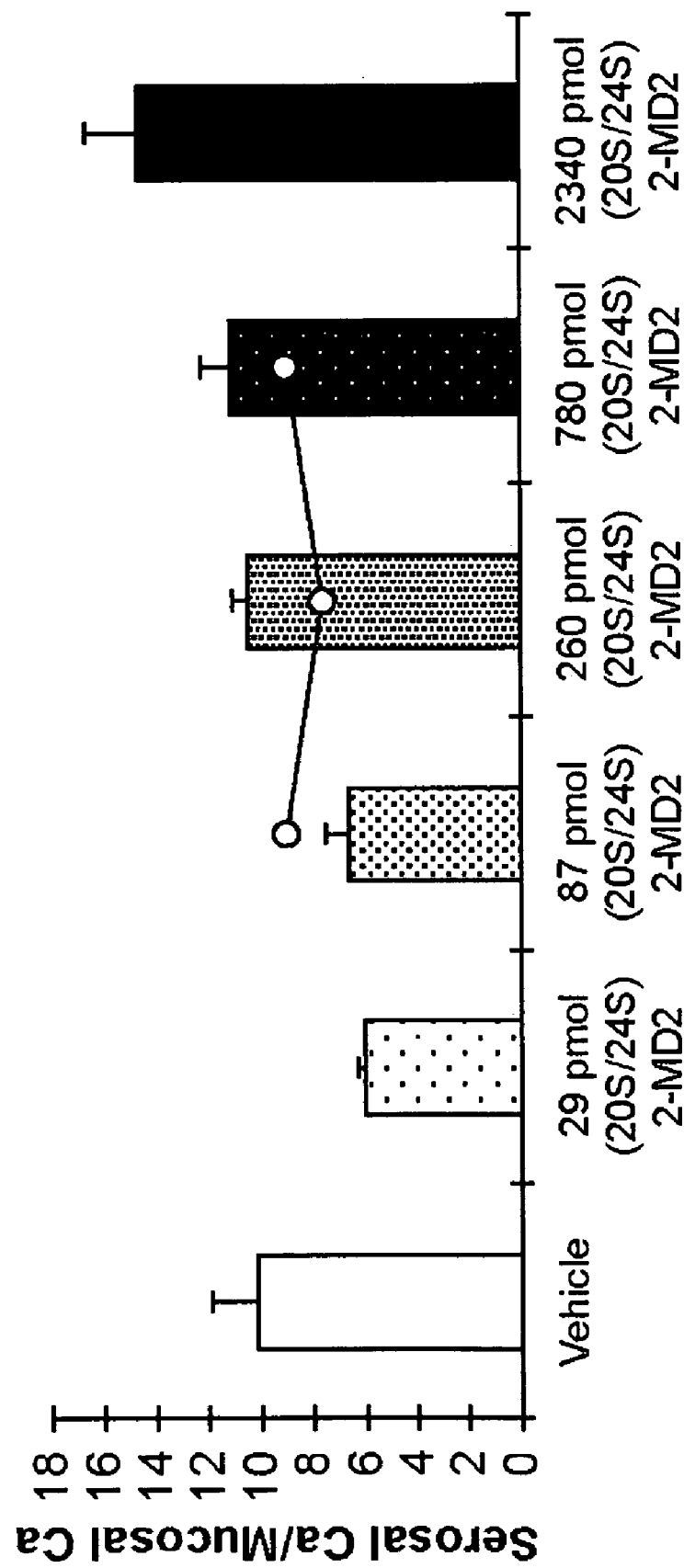

2-Methylene-19-nor-(20S-24S)-1α,25-dihydroxyvitamin $D_2$ is almost equal to the native hormone in binding to the vitamin D receptor as shown in FIG. 1. 2-Methylene-19-nor-(20S-24S)-1α,25-dihydroxyvitamin $D_2$ is also almost equal to the native hormone in inducing differentiation of HL-60 cells (FIG. 2), and it is slightly more effective than 1,25-(OH)$_2D_3$ in causing transcription, as shown in FIG. 3. 2-Methylene-19-nor-(20S-24S)-1α,25-dihydroxyvitamin $D_2$ has bone calcium mobilizing activity comparable to 1,25(OH)$_2D_3$ (FIG. 4), and the compound does retain some ability to elevate intestinal calcium transport (FIG. 5). This compound will find use as an effective therapy for secondary hyperparathyroidism of dialysis patients and calcium imbalance disorders such as, but not limited to, osteopenia, osteoporosis, and the like. It may also be used for the treatment of malignancy of colon, prostate, and breast, and can be used in the therapy of autoimmune diseases such as multiple sclerosis, diabetes type 1 and type 2 diabetes, inflammatory bowel diseases, lupus, rheumatoid arthritis and Lou Gehrig's Disease.

The compounds of the invention are also useful in preventing or treating obesity, inhibiting adipocyte differentiations, inhibiting SCD-1 gene transcription, and/or reducing body fat in animal subjects. Therefore, in some embodiments, a method of preventing or treating obesity, inhibiting adipocyte differentiations, inhibiting SCD-1 gene transcription, and or reducing body fat in animal subject includes administering to the animal subject, an effective amount of the compound or a pharmaceutical composition that includes the compound. Administration of the compound or the pharmaceutical composition to the subject inhibits adipocyte differentiation, inhibits gene transcription, and/or reduces body fat in the animal subject.

For treatment purposes, the compounds defined by formula I, formula IA, and formula IB may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, anti-oxidants, binders, coloring agents or emulsifying or taste-modifying agents. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is hereby incorporated by reference in its entirety and for all purposes as if fully set forth herein.

The compounds may be administered orally, topically, parenterally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from 0.001 μg to about 1 mg per day of the compound are appropriate for treatment purposes. In some such embodiments an appropriate and effective dose may range from 0.01 μg to 1 mg per day of the compound. In other such embodiments an appropriate and effective dose may range from 0.1 μg to 500 μg per day of the compound. Such doses will be adjusted according to the type of disease or condition to be treated, the severity of the disease or condition, and the response of the subject as is well understood in the art. The compound may be suitably administered alone, or together with another active vitamin D compound.

Compositions for use in the invention include an effective amount of 2-methylene-19-nor-(20S-24S)-1α,25-dihydroxyvitamin $D_2$ as the active ingredient, and a suitable carrier. An effective amount of the compound for use in accordance with some embodiments of the invention will generally be a dosage amount such as those described herein, and may be administered topically, transdermally, orally, nasally, rectally, or parenterally.

The compound of formula IA and formula IB may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The compound may be formulated as creams, lotions, ointments, aerosols, suppositories, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100 microns.

The formulations may conveniently be presented in dosage unit form and may be prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

All references cited herein are specifically incorporated by reference in their entireties and for all purposes as if fully set forth herein.

It is understood that the invention is not limited to the embodiments set forth herein for illustration, but embraces all such forms thereof as come within the scope of the following claims.

What is claimed is:

1. A compound having the formula I

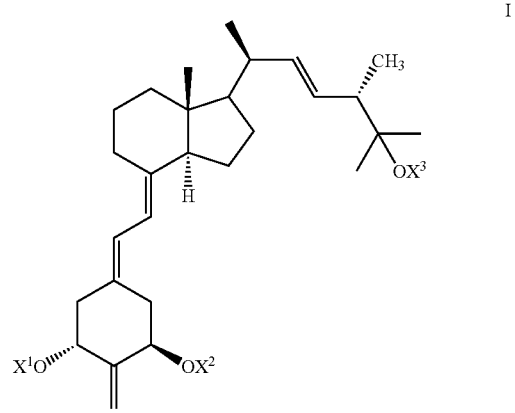

wherein $X^1$, $X^2$, and $X^3$ are independently selected from H and hydroxy protecting groups.

2. The compound of claim 1, wherein $X^1$ and $X^2$ are both hydroxy protecting groups.

3. The compound of claim 2, wherein $X^1$ and $X^2$ are both t-butyldimethylsilyl groups.

4. The compound of claim 1, wherein $X^1$, $X^2$, and $X^3$ are all H and the compound has the formula IA

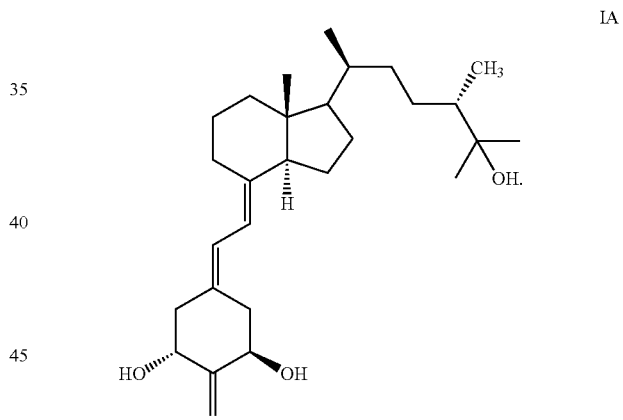

5. A pharmaceutical composition, comprising an effective amount of the compound of claim 4 and a pharmaceutically acceptable carrier.

6. The pharmaceutical composition of claim 5 wherein the effective amount comprises from about 0.01 μg to about 1 mg of the compound per gram of the composition.

7. The pharmaceutical composition of claim 5 wherein the effective amount comprises from about 0.1 μg to about 500 μg of the compound per gram of the composition.

8. A method of treating a subject suffering from a biological condition, comprising administering an effective amount of the compound of claim 4 to the subject, wherein the biological condition is selected from psoriasis; leukemia; colon cancer; breast cancer; prostate cancer; multiple sclerosis; lupus; diabetes mellitus,; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; or osteoporosis.

9. The method of claim 8, wherein the biological condition is psoriasis.

10. The method of claim 8, wherein the biological condition is selected from leukemia, colon cancer, breast cancer, or prostate cancer.

11. The method of claim 8, wherein the biological condition is selected from multiple sclerosis, lupus, diabetes mellitus host versus graft reaction, or rejection of organ transplants.

12. The method of claim 8, wherein the biological condition is selected from rheumatoid arthritis, asthma, or inflammatory bowel diseases selected from celiac disease, ulcerative colitis and Crohn's disease.

13. The method of claim 8, wherein the biological condition is selected from wrinkles, lack of adequate skin firmness, lack of adequate dermal hydration, or insufficient sebum secretion.

14. The method of claim 8, wherein the compound is administered orally to the subject.

15. The method of claim 8, wherein the compound is administered parenterally to the subject.

16. The method of claim 8, wherein the compound is administered transdermally to the subject.

17. The method of claim 8, wherein the compound is administered topically to the subject.

18. The method of claim 8, wherein the compound is administered in a dosage of from 0.01 μg per day to 1 mg per day.

19. The compound of claim 1, wherein $X^1$, $X^2$, and $X^3$ are all H and the compound has the formula IB

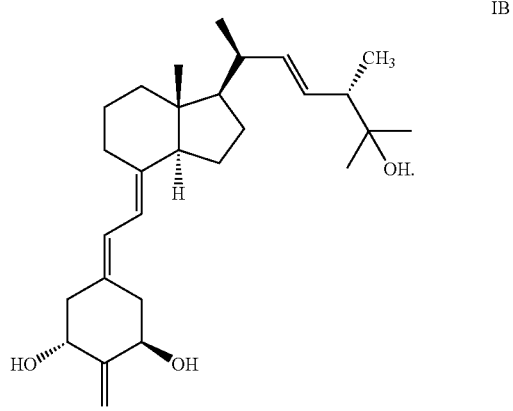

* * * * *